(12) United States Patent
Breit

(10) Patent No.: US 10,264,645 B2
(45) Date of Patent: Apr. 16, 2019

(54) LIGHT AND METHOD FOR OPERATING A LIGHT

(71) Applicant: Marc Breit, Kleinblittersdorf (DE)

(72) Inventor: Marc Breit, Kleinblittersdorf (DE)

( * ) Notice: Subject to any disclaimer, the term of this patent is extended or adjusted under 35 U.S.C. 154(b) by 0 days.

(21) Appl. No.: 15/510,744

(22) PCT Filed: Sep. 15, 2015

(86) PCT No.: PCT/EP2015/071140
§ 371 (c)(1),
(2) Date: Mar. 13, 2017

(87) PCT Pub. No.: WO2016/041994
PCT Pub. Date: Mar. 24, 2016

(65) Prior Publication Data
US 2017/0257923 A1     Sep. 7, 2017

(30) Foreign Application Priority Data

Sep. 15, 2014 (DE) .......... 10 2014 013 781
Sep. 15, 2014 (DE) .......... 20 2014 007 579 U

(51) Int. Cl.
*H05B 33/08* (2006.01)
*G01N 21/88* (2006.01)
(Continued)

(52) U.S. Cl.
CPC ..... *H05B 33/0857* (2013.01); *G01N 21/8803* (2013.01); *G01N 21/8806* (2013.01);
(Continued)

(58) Field of Classification Search
CPC ............ H05B 33/0857; H05B 33/0863; H05B 33/0884; H05B 37/02; H05B 37/029;
(Continued)

(56) References Cited

U.S. PATENT DOCUMENTS 5,670,786 A * 9/1997 Meyer ............... A61N 5/06
250/494.1
6,132,072 A 10/2000 Turnbull et al.
(Continued)

FOREIGN PATENT DOCUMENTS

DE      10326369 A1    1/2005
DE    102004043295 A1   3/2006
(Continued)

*Primary Examiner* — Haissa Philogene
(74) *Attorney, Agent, or Firm* — Lucas & Mercanti, LLP; Klaus P. Stoffel

(57) ABSTRACT

A light, in particular for testing workpiece surfaces using a fluorescent marking device, which light has at least two lighting elements that emit electromagnetic radiation with different wavelength ranges. The intensity with which the lighting element irradiates can be adjusted separately for at least one of the lighting elements. Expediently, the light is configured to increase or reduce the intensity of at least one of the lighting elements and at the same time to keep the intensity of at least one other of the lighting elements constant, or to reduce it or increase it in the opposite way to the first-mentioned lighting element. The light is configured to adjust the intensity at such a speed that the human eye can adapt to a change in the intensity during the adjustment without adverse effects on the person's sight.

20 Claims, 5 Drawing Sheets

(51) Int. Cl.
*G01N 21/91* (2006.01)
*F21V 1/00* (2006.01)
*F21V 29/70* (2015.01)

(52) U.S. Cl.
CPC ...... *H05B 33/0893* (2013.01); *F21L 2001/00* (2013.01); *F21V 29/70* (2015.01); *G01N 21/91* (2013.01); *G01N 2021/8835* (2013.01); *G01N 2201/06153* (2013.01)

(58) Field of Classification Search
CPC ............ H05B 37/0272; H05B 37/0254; H05B 33/0896; G01N 21/8803; G01N 21/8806; G01N 21/91; G01N 2201/06153; G01N 2201/0624; G01N 2021/8835; G01N 2021/8845; F21L 2001/00
See application file for complete search history.

(56) References Cited

U.S. PATENT DOCUMENTS

| | | | |
|---|---|---|---|
| 6,600,175 B1 * | 7/2003 | Baretz | H01L 33/50 257/100 |
| 7,301,346 B2 | 11/2007 | Annighoefer | |
| 7,307,770 B2 * | 12/2007 | Wilkinson | G03H 1/22 359/2 |
| 8,100,552 B2 * | 1/2012 | Spero | B60Q 1/04 362/227 |
| 8,264,172 B2 * | 9/2012 | Valois | H05B 37/0254 315/291 |
| 8,497,871 B2 * | 7/2013 | Zulch | G01J 3/504 345/589 |
| 8,516,722 B2 | 12/2013 | Duerr | |
| 8,998,444 B2 * | 4/2015 | Roberts | F21K 9/00 313/503 |
| 9,797,567 B2 * | 10/2017 | Kastner-Jung | F21S 10/02 |
| 2007/0081210 A1 | 4/2007 | Wilkinson | |
| 2014/0225514 A1 | 8/2014 | Pickard | |
| 2017/0257923 A1 * | 9/2017 | Breit | G01N 21/8803 |
| 2018/0252653 A1 * | 9/2018 | Breit | G01N 21/6447 |

FOREIGN PATENT DOCUMENTS

| | | |
|---|---|---|
| DE | 102006004995 A1 | 10/2006 |
| DE | 102004043295 B4 | 4/2007 |
| EP | 1623213 B1 | 11/2010 |

* cited by examiner

LIGHT AND METHOD FOR OPERATING A LIGHT

The present application is a 371 of International application PCT/EP2015/071140, filed Sep. 15, 2015, which claims priority of DE 10 2014 013 781.3, filed Sep. 15, 2014, and DE 20 2014 007 579.4, filed Sep. 15, 2014, the priority of these applications is hereby claimed and these applications are incorporated herein by reference.

BACKGROUND OF THE INVENTION

The invention relates to a luminaire, in particular for testing workpiece surfaces, which comprises at least two illuminants which emit electromagnetic radiation in different wavelength ranges.

The invention furthermore relates to a method for operating a luminaire, in particular for testing workpiece surfaces, if appropriate using a fluorescent marking medium.

DE 10 2004 043 295 B4, EP 1 623 213 B1 and U.S. Pat. No. 8,616,722 B2 disclose luminaires of the type mentioned in the introduction which comprise LEDs that emit white light and ultraviolet radiation. They are used for visual inspections of workpiece surfaces, in particular for detecting contaminants, for penetrant testing and for fluorescent magnetic powder testing. During visual inspection, in particular during testing of workpiece surfaces according to the fluorescent penetrant method, a fluorescent medium is used to make defects on workpiece surfaces visible by excitation with ultraviolet radiation. The inspection is usually carried out in the dark, with ambient illuminance of less than 20 lux, because human beings have higher contrast sensitivity in visual perception in the case of mesopic vision (twilight vision) and scotopic vision (night vision) and better testing can be carried out when there is high contrast between the surface to be examined and the excited fluorescences. What is problematic is that when carrying out the test methods by means of the known luminaires, when changing over between illumination with white light, which is used to inspect and assess defects found on the workpiece under the ultraviolet radiation, and illumination with ultraviolet radiation, a comparatively large change in brightness occurs to which the eyes have to adjust. Since the test is often accompanied by frequent changeover, the eyes are subjected to a comparatively great burden.

SUMMARY OF THE INVENTION

The invention is based on the object of providing a luminaire of the type mentioned in the introduction with which the test of the workpiece surfaces can be carried out better.

A luminaire which achieves this object is characterized in that an intensity with which the illuminant radiates is adjustable for at least one of the illuminants.

The invention affords the possibility of coordinating with one another the intensities with which the respective illuminants radiate, when changing over from one of the illuminants to another of the illuminants or when feeding one of the illuminants to another, in such a way that abrupt changes in intensity are avoided. Advantageously, with such a coordination the eyes can adapt better to the change in intensity and better visual perception can be achieved as a result.

Sudden, possibly great changes in intensity such as occur in the case of the known luminaires in particular when the white light is switched on and off, primarily with low ambient brightness, and which are very unpleasant and tiring for the eyes and can even damage the eyes can be avoided.

Expediently, for the at least one illuminant the intensity is adjustable separately from the other illuminant.

In one embodiment of the invention, one of the illuminants is provided for emitting visible light, preferably white light, and another of the illuminants is provided for emitting ultraviolet radiation, infrared radiation and/or blue-violet light. Preferably, the radiation emitted by the illuminant for emitting visible light comprises a wavelength range of between 380 and 780 nm, that of the illuminant for emitting ultraviolet radiation comprises a wavelength range of between 200 and 400 nm, that of the illuminant for emitting infrared radiation comprises a wavelength range of between 780 nm and 50 μm, and that of the illuminant for emitting blue-violet light comprises a wavelength range of between 380 and 490 nm.

During visual inspection, as explained above, the ultraviolet radiation is used to find defects or the like on a surface of a workpiece with the aid of a fluorescent medium, and under the white light, if appropriate with simultaneous irradiation with ultraviolet radiation, the workpiece is aligned and/or defects or the like found under the ultraviolet radiation are inspected, analyzed, interpreted and/or assessed.

Expediently, the intensity with which the respective illuminant radiates is controllable and/or regulatable over the entire power range of the illuminant between a minimum intensity, at which the illuminant preferably emits no radiation, and a maximum intensity, which is preferably settable and can be varied, if appropriate, within certain limits.

In one configuration of the invention, the luminaire is configured to increase or to reduce the intensity of at least one of the illuminants and at the same time to keep constant the intensity of at least one other of the illuminants or to reduce or increase it oppositely to the first-mentioned illuminant.

By means of such changes in intensity, it is possible firstly to place one illuminant in relation to the other and secondly to fade across from one illuminant to the other and thus from one irradiation in one wavelength range to another.

Expediently, the intensities of individual or all of the illuminants are adjustable separately.

In a further configuration of the invention, the luminaire is configured in such a way that the speed at which the intensity is changed is dependent on the intensity with which the illuminant radiates.

In one particularly preferred embodiment of the invention, the luminaire is provided in such a way that the speed of the change in the intensity with which the respective illuminant radiates is lower in intensity ranges in which radiation is effected with comparatively low intensity, compared with intensity ranges in which radiation is effected with comparatively high intensity.

While it would be conceivable to change the speed of the change in intensity linearly as a function of time or proportionally to the intensity, said speed is preferably changed as an exponential function of the intensity.

With the different speeds of the change in intensity, the change in intensity in the different brightness ranges is adapted to the adaptability of the eye and it is taken into account that the eye in different intensity ranges has a different sensitivity to changes in intensity and reacts to changes in intensity more sensitively in the dark than in the light. The sensitivity is not linear with respect to the intensity, for instance, but rather is described by the Weber-Fechner law or Stevens' power function, which both show that the sensitivity of the eye is proportional to the logarithm of the intensity of the radiation. Accordingly, in ranges of lower radiation intensity, the intensity can be changed only at comparatively low speeds without bringing about a comparatively great stimulation of the eyes, while in ranges of higher radiation intensity, the intensity can be changed more rapidly without being unpleasant.

In one embodiment of the invention, the luminaire is configured for adjusting the intensity at a speed such that the human eye can adapt to a change in the intensity during the adjustment without or with only slight impairment of visual perception, in particular visual acuity, preferably in such a way that a defect found under one of the types of illumination can then be kept in view during the adjustment of the luminaire from one illuminant to the other. There are no difficulties in finding a defect again upon illumination with white light once said defect has been found under UV illumination, said difficulties often occurring with the use of the conventional luminaires. As a result, the visual test can be carried out more rapidly and more accurately than with the known luminaires.

In a further configuration of the invention, the luminaire is configured for adjusting the intensity in such a way that the change in the intensity is perceived by the human eye as uniform, in particular without intensity jumps. The change in intensity is not perceived as unpleasant in the case of such a change and protects the eyes.

Expediently, the intensity is adjustable between 0% and 100% of a maximum intensity provided, which is preferably 20 to 2000 lux, in such a way that the human eye can adapt to a change in the intensity during the adjustment without impairment of the faculty of sight and/or that the change in the intensity is perceived as uniform by the human eye. While it would be conceivable to provide such an adjustability only in sections for specific intensity ranges, it is preferably provided over the entire intensity range in order to enable pleasant work with the luminaire.

The maximum intensity is expediently settable, preferably separately for each of the luminaires, in order that the luminaire can be adapted to individual requirements.

In a further embodiment of the invention, the average speed of the change in the intensity of the white light is between 5 lux/s and 500 lux/s.

Expediently, the following durations are provided for establishing the intensity of the white light:
increase in the intensity from 0 to 20 lux/reduction of the intensity from 20 to 0 lux: duration >1-1.5 seconds
increase in the intensity from 0 to 50 lux/reduction of the intensity from 50 to 0 lux: duration >1.5-2.5 seconds
increase in the intensity from 0 to 100 lux/reduction of the intensity from 100 to 0 lux: duration >2-3 seconds
increase in the intensity from 0 to an intensity >100 lux/reduction of the intensity from an intensity >100 lux to 0 lux: duration >2.5 seconds.

In the stated speed ranges, it is possible to work sufficiently rapidly with the luminaire; excessive fatigue of the eyes is avoided, however, and the faculty of sight is not impaired upon a change in the intensity and the changes in intensity are perceived as uniform.

In order that an adaptation of the eye to the white light when setting the illuminant for white light from a switched-off state, in which the illuminant does not radiate, is configured as pleasantly as possible, the luminaire is expediently configured in such a way that the illuminant for white light can be set to intensities which are <1%, preferably <0.5%, particularly preferably <0.1%, of a maximum intensity provided for the white light.

In a particularly preferred embodiment of the invention, the illuminant for white light can be adjusted from the switched-off state in steps that are <1 lux, preferably <0.5 lux.

The luminaire can be configured in such a way that, from the two last-mentioned setting possibilities, i.e. the percentage dependence on the maximum intensity and the steps in 1 or 0.5 lux, said luminaire chooses the possibility for which smaller steps are carried out.

Preferably, the luminaire is configured in such a way that the speed or the speeds of the change in intensity is or are variable, preferably within certain limits, in order to be able to adapt the latter individually.

Expediently, at least one of the illuminants is formed by a discharge lamp or/and by at least one light-emitting semiconductor diode (LED), wherein the illuminant(s) is (are) preferably provided with a filter for setting the respective wavelength range.

Expediently, the luminaire comprises a control and/or regulation device for adjusting the intensities. The control and/or regulation device preferably comprises at least one constant-current control which functions on the basis of electrical and electronic circuits and control loops. The luminaires, in particular the LEDs, can be operated particularly efficiently as a result because, by means of the constant-current control, the operating current of the respective illuminant, in particular of the LED or of the LED circuit, can be measured and kept constant within narrow limits. Expediently, the constant-current control can generate the constant current from an AC and/or DC voltage.

The intensity of the LED is preferably changed using pulse width modulation. For this purpose, the luminaire preferably comprises a pulse width modulation control.

Furthermore, the control and/or regulation device can comprise a regulation which can reduce or switch off the power of the luminaire or of individual parts of the luminaire in a temperature-dependent manner in order to protect the luminaire, in particular the illuminants and/or the control and/or regulation unit, against overheating. For cooling purposes, in addition or as an alternative thereto the luminaire could be provided with a fan, which is preferably controllable and/or regulatable by means of the control and/or regulation device.

The luminaire is expediently configured in such a way that the intensity of the illuminant, preferably emitting white light, is increased during an actuation of the operating element and is reduced upon release of the operating element.

Alternatively, provision could be made for the intensity of the illuminant, preferably for white light, to be increased automatically up to the maximum intensity provided, in a manner triggered by actuation of the operating element, and, after the maximum intensity has been attained, for the intensity to be reduced again automatically or by renewed actuation of the operating element, preferably down to a minimum value provided, at which preferably no radiation is emitted.

Expediently, the luminaire is configured for indicating an operating state of at least one of the illuminants. The operating state preferably comprises the intensity with which the illuminant emits the radiation, and/or a duration during which the illuminant emits radiation, preferably with a predetermined intensity. The indication of the duration serves, in particular, to ensure compliance with time periods which are predefined in the abovementioned testing of the workpiece surfaces and which are provided for an adaptation of the eye to specific intensities. As an alternative or in addition thereto, provision may be made for the luminaire to indicate whether or not the respective illuminant is emitting radiation, i.e. in particular whether said illuminant is switched on or off, and the duration for which said illuminant has been in the respective operating state. Advantageously, it is possible to indicate whether enough time to enable the eyes to adapt to the respective intensity has elapsed after attainment of the respective operating state. Preferably, the standard values for eye adaptation durations that are provided for the respective operating states are provided in the luminaire.

In one configuration of the invention, the luminaire according to the invention is used as follows. Firstly, preferably in the dark or with very low ambient brightness, the illuminant that emits UV radiation is switched on. In this case, the intensity of the emitted radiation is increased to a predetermined target intensity preferably at one of the above-explained speeds of the change in intensity. However, it can also be set abruptly to the target intensity since sudden changes of illumination resulting from the UV radiation are less unpleasant to the eye. A workpiece surface can then be examined under UV radiation. In order also to inspect the workpiece surface under visible light, the illuminant provided for emitting white light is switched on and the intensity is increased to a predetermined target intensity, preferably at one of the speeds explained above. Optionally, the UV illuminant can be switched off upon a specific intensity of the white light illuminant being attained or during the increase in the intensity or the intensity can be reduced, preferably at one of the speeds explained above. Expediently, for a further examination under UV radiation, subsequently the UV illuminant is switched on again and the intensity of the radiation of the UV illuminant is increased, preferably at one of the speeds explained above. Afterward or at the same time, the intensity of the white light luminaire, preferably as described above, is increased again to a predetermined target intensity at which the workpiece surface is intended to be inspected with visible light.

It goes without saying that the luminaire is configured to automatically carry out the above-described changes in the intensities of the respective illuminants, if appropriate in response to a command input by means of an operating element.

In one configuration of the invention, the luminaire comprises a monitoring device that is configured for identifying an operational fault, in particular a defect of one of the illuminants or of other components of the luminaire, and preferably is provided for deactivating the luminaire upon finding an operational fault. The monitoring device can furthermore be configured for indicating the operational fault.

In a further embodiment of the invention, the luminaire comprises an adjusting device provided for regulating a power of the radiation emitted by the respective illuminant depending on a temperature of the apparatus. Advantageously, a reduction of the intensity that occurs as the temperature rises can be compensated for as a result.

Expediently, a size of a region which is irradiatable by means of the luminaire is adjustable. Preferably, provision is made of a first setting, in which a comparatively small region is irradiatable and which serves for a focused observation, and a further setting, with which a larger region can be irradiated.

The luminaire expediently comprises at least one housing which is preferably provided for accommodating the illuminants, at least one operating element, at least one optical system which preferably comprises at least one lens, and/or at least one cooling medium, preferably a fan, a heat exchanger and/or a cooling plate.

In one configuration of the invention, the luminaire is usable in mobile and/or stationary use. It can be a hand luminaire and/or a standard luminaire or a luminaire that can be fixedly installed for example on a mount or a wall.

While in one particularly preferred embodiment of the invention a device for operating the luminaire is integrated into the housing, it would also be conceivable to provide said device outside the housing, wherein the luminaire preferably comprises at least one housing for the illuminants, at least one switchgear cabinet or switchgear housing and/or at least one operating element. Expediently, the operating device comprises at least one manually actuatable or foot-actuatable operating element by means of which the intensity of at least one of the illuminants is variable.

The operating element, which is preferably formed by a pushbutton or a rotary regulator, expediently serves to switch the respective illuminants on or off or to instigate control and/or regulation of the intensities with which the respective illuminants radiate.

The power supply of the luminaire can be effected by at least one external or integrated DC and/or AC source.

The term luminaire is intended also to encompass a luminaire system.

The invention is explained in greater detail below on the basis of an exemplary embodiment and the accompanying drawings relating to the exemplary embodiment, in which:

DETAILED DESCRIPTION OF THE INVENTION

Figure 1:
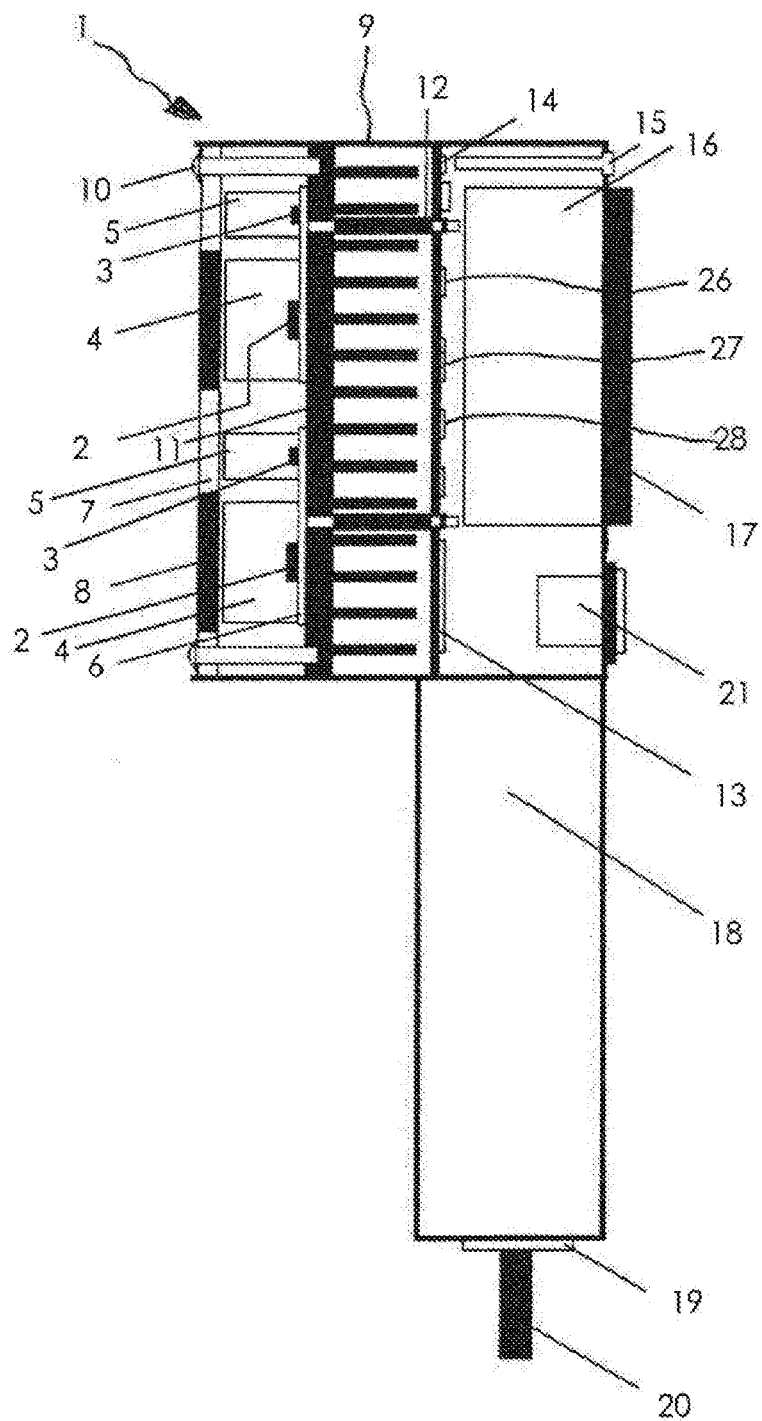
FIG. 1 shows a luminaire according to the invention in lateral section.
Figure 2:
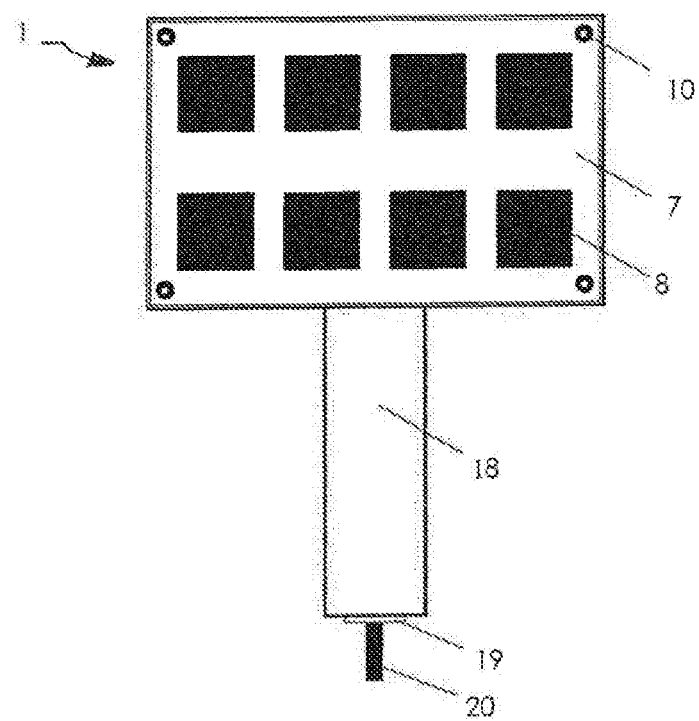
FIG. 2 shows a front view of the luminaire according to FIG. 1.
Figure 3:
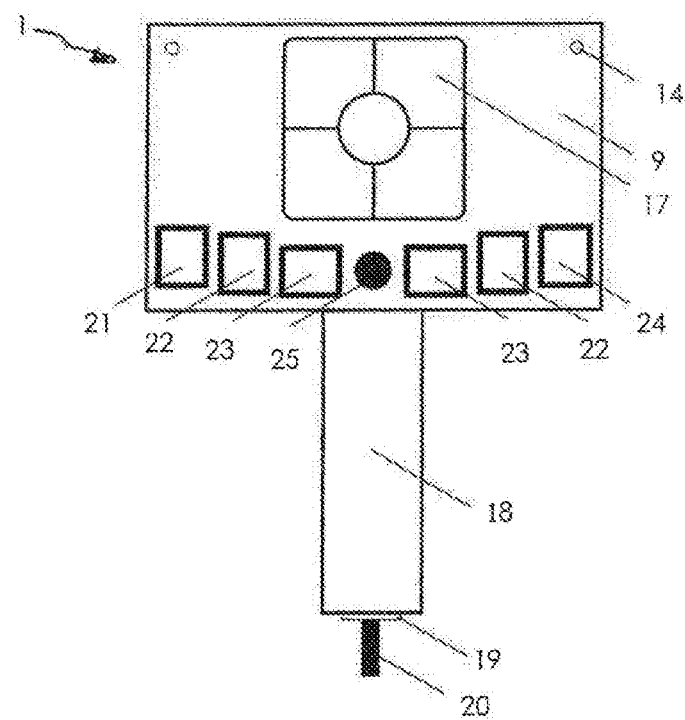
FIG. 3 shows a rear view of the luminaire according to FIG. 1.

A luminaire 1 according to the invention as illustrated in FIGS. 1 to 3 comprises eight UV LEDs 2 provided for emitting UV radiation (wavelength range 200-400 nm) and eight white light LEDs 3 provided for emitting white light (wavelength range 380-780 nm). Optical components 4, 5 are arranged in front of the LEDs 2, 3 in order to influence respective beam paths emerging from the LEDs. A front screen 7 is arranged downstream of the optical components 4, 5 as viewed in the radiation direction, said front screen being connected to a housing 9 of the luminaire 1 via fixing means 10 and being provided with filters 8 for each of the UV LEDs 2.

The LEDs 2, 3 are soldered onto a carrier board 6 arranged on a heat sink 11. The heat sink 11 is connected via spacer bolts 12 to a printed circuit board 13 carrying a plurality of electronic components. Furthermore, an indicator LED 14 is arranged on the printed circuit board 13, said indicator LED being provided for indicating an operating state of the luminaire 1, as explained in greater detail below. An optical waveguide 15 is arranged between a rear side of the housing 9 and the indicator LED 14, by means of which optical waveguide radiation can be guided from the indicator LED 14 to the rear side.

The electronic components form a regulation and/or control device 26 configured for controlling and/or regulating the intensities with which the LEDs 2, 3 radiate.

The electronic components furthermore form a monitoring device 27 provided for identifying faults during the operation of the luminaires 1. The monitoring device 27 is connected in such a way that it can deactivate the luminaire 1 upon an operational fault being found, for example upon failure of one of the LEDs 2, 3. Furthermore, it can be provided, for example by indicating a code, for characterizing the operational fault via the indicator LED or some other indicator device.

Furthermore, an adjusting device 28 is formed by the electronic components on the printed circuit board 13, said adjusting device being provided for regulating powers with which the LEDs 2, 3 radiate depending on a temperature of the luminaire 1 in order to be able to compensate for a change in the current intensity that occurs upon heating of the luminaire 1, in order to regulate the respective intensities to the values provided.

A fan 16 is provided for cooling the luminaire, by means of which fan air can be blown onto the printed circuit board 13 and the heat sink 11. The housing 9 is provided on its rear side with a ventilation grille 17, which is provided for accommodating a filter and through which the air is drawn in by means of the fan 16.

The luminaire 1 furthermore comprises a handle 18, at the lower end of which a line 20 is led via a strain reliever 19, via which line the luminaire 1 can be supplied with energy and controlled, if appropriate.

As can be gathered from FIG. 3, in particular, the luminaire 1 is provided on its rear side with pushbuttons 21, 22, 23, 24 and a rotary regulator 25, which are provided for controlling intensities with which the LEDs 2, 3 emit light, and which interact with the control and/or regulation device 26.

The control and regulation device 26 is provided for varying intensities with which the UV LEDs 2 and the white light LEDs 3 radiate separately from one another by means of pulse width modulation.

The control and regulation device 26 changes the intensities at a speed such that the human eye can adapt to the changing intensity without or with only slight impairment of visual perception, in particular visual acuity, such that a defect found can be kept in view upon the change in the intensity. Furthermore, the intensities are changed in such a way that the human eye perceives the change in intensity uniformly, i.e. without intensity jumps. In order, on the one hand, to enable a changeover from an illumination with UV radiation to an illumination with white light in a manner that causes as little fatigue as possible and, on the other hand, to carry out the changeover of the last-mentioned prerequisite as rapidly as possible, the control and regulation device 26 is programmed in such a way that the respective intensity, in accordance with the adaptability of the human eye, is changed comparatively slowly at low intensity and more rapidly at comparatively high intensity. In this case, a speed at which the respective intensity is changed can be proportionally or exponentially dependent on the respective intensity or be changed linearly as a function of time.

Figure 4:
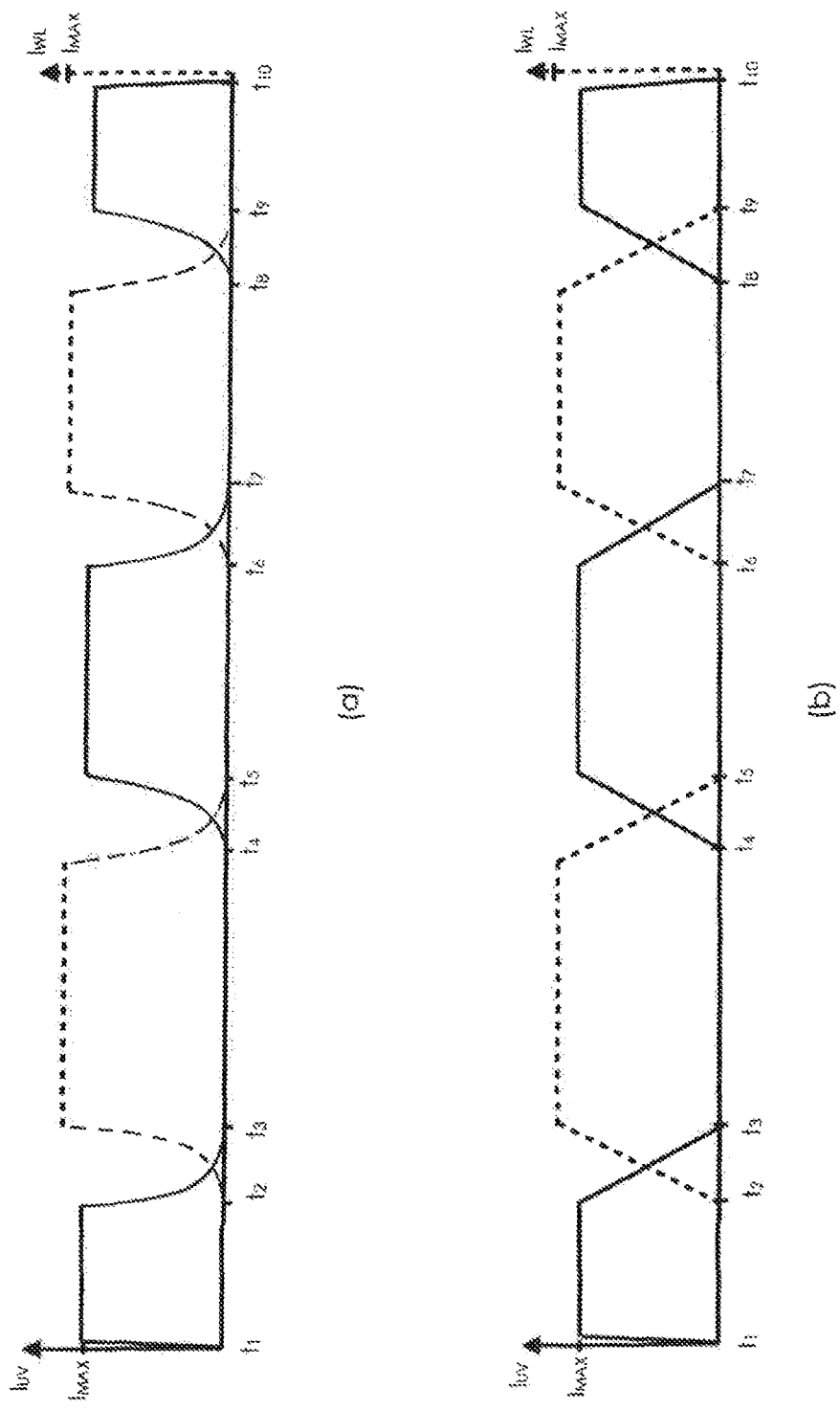
FIGS. 4 to 6 show diagrams elucidating the invention.

Actuation of the pushbuttons 21, 22, 23, 24 causes the control and regulation device 26 to change the intensities of the UV LEDs and of the white light LEDs 3, as explained below with reference to FIGS. 4 to 6, which show diagrams illustrating the temporal profile of the intensities of the UV LEDs 2 (Y-axis $I_{UV}$ plotted on the left-hand side) and of the white light LEDs 3 (Y-axis $I_W$ plotted on the right-hand side).

$1^{st}$ Example (Cf. FIG. 4)

At the point in time $t_1$, the pushbutton 21 is actuated and, as a result, the UV LED 2 is switched on and emits light with a target intensity $I_{MAX}$ at which a workpiece can be examined.

At the point in time $t_2$, actuation of one of the pushbuttons 22 causes fading across from radiation with the UV LED 2 to radiation by means of the white light LED 3, that is to say that the intensity with which the white light LED 3 radiates, as explained above, is increased to a target intensity $I_{MAX}$ and at the same time the intensity with which the UV LED 2 radiates is reduced to an extent such that it no longer radiates. At the point in time $t_3$, the target intensity $I_{MAX}$ of the white light LED 3 is attained and the intensity of the UV LED is reduced to zero. The workpiece can then be inspected under white light.

If the intention is then to carry out a renewed examination also under UV illumination, the pushbutton 22 is released again, with fading across to illumination by means of the UV LED 2 (points in time $t_4$ and $t_5$), and renewed actuation of the pushbutton 22 makes it possible to fade across to white light again (points in time $t_6$ and $t_7$).

Upon renewed fading across to UV light, the pushbutton 22 is released again (points in time $t_8$ and $t_9$).

In order to switch off the UV LED 2, the pushbutton 21 is actuated again.

It goes without saying that fading across back and forth between the UV LED 2 and white light LED 3 can be effected as often as desired for examining the workpiece.

It may be provided that fading across to a radiation only by means of white light is carried out only as long as one of the pushbuttons 22 is actuated and, when one of the pushbuttons 22 is released, conversely, the intensity of the white light LED 3 is reduced again and that of the UV LED is increased to the target intensity.

Advantageously, a location on the workpiece, e.g. a defect observed under ultraviolet radiation or under white light, can be kept in view during fading-across as well. In both changeover directions, i.e. from white light to ultraviolet radiation and vice versa, the respective changes in intensity are perceived as a film. Since the changes in intensity are perceived at speeds such that the eyes can adapt thereto, visual perception, in particular visual acuity, is not impaired or is only slightly impaired.

As illustrated in FIG. 4a, the intensities of the UV LED 2 and of the white light LED 3 can be changed in such a way that the intensities are changed more rapidly at higher intensities than at low intensities. As explained above, the human eye can then adapt better to the changing intensities.

However, it would also be conceivable to change the intensities linearly as a function of time, as shown in FIG. 4b.

It goes without saying that the different for changing intensities could also be combined with one another. In this regard, it might be possible e.g. to change only the intensity of the white light LED 3 depending on the magnitude of the intensity and to change the intensity of the UV LED 2 proportionally to time.

Figure 5:
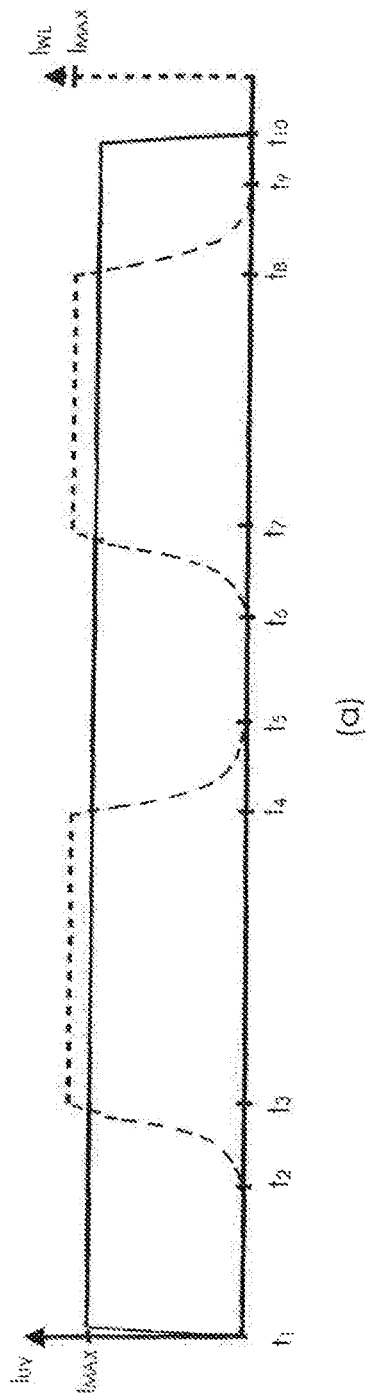
Figure 5:
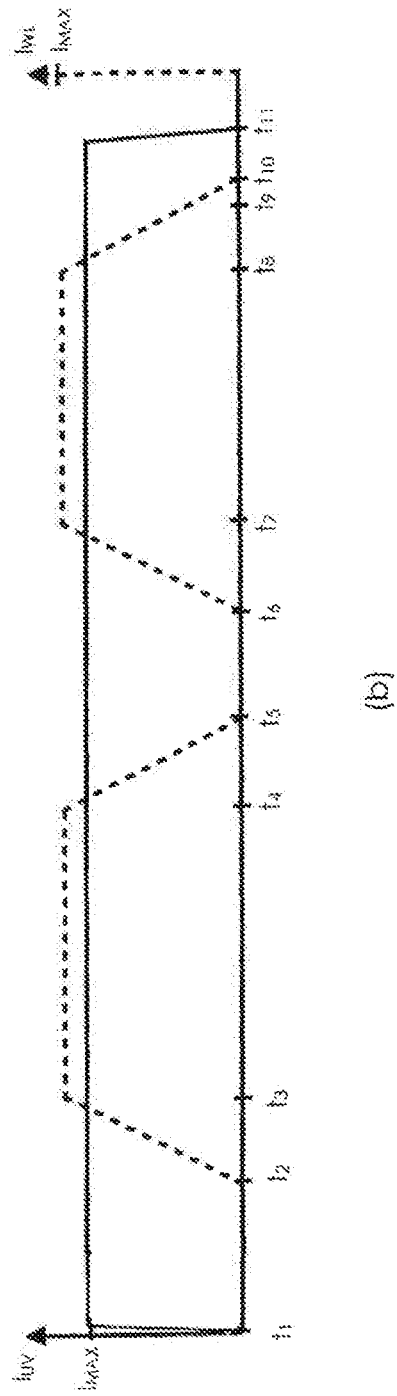

$2^{nd}$ Example (FIG. 5)

At a point in time $t_1$, by means of the actuation of the pushbutton 21, the UV LED 2 is switched on and the intensity is set to the target intensity $I_{MAX}$. By means of the actuation of one of the pushbuttons 23 (point in time $t_2$), the white light LED 3 is set in addition to the UV LED 2, wherein the intensity with which the white light LEDs radiates, as explained above, is increased gradually to a target value $I_{MAX}$ until it attains the latter at a point in time $t_3$, and the intensity with which the UV LED 2 emits light remains constant. In the same way as explained above, the intensity of the white light LED 3 is increased and the intensity is kept constant at $I_{MAX}$ only as long as the pushbutton 23 is kept pressed, and release (point in time $t_4$) of the pushbutton 23 causes the intensity of the white light LED 3 to be reduced again until it no longer radiates from the point in time $t_5$ on. Afterward, as necessary, the white light LED 3 can be switched again to the UV LED 2 (points in time $t_6$ to $t_8$ and $t_{10}$). Once the examination of the workpiece has ended, the UV LED is switched off by the actuation of the pushbutton 21 (points in time $t_9$ and $t_{11}$).

As explained above with reference to FIG. 5, in this example as well the white light LED 3 can be varied at different speeds depending on the respective intensity (FIG. 5*a*) or the intensity can be implemented as a linear function of time (FIG. 5*b*).

Figure 6:
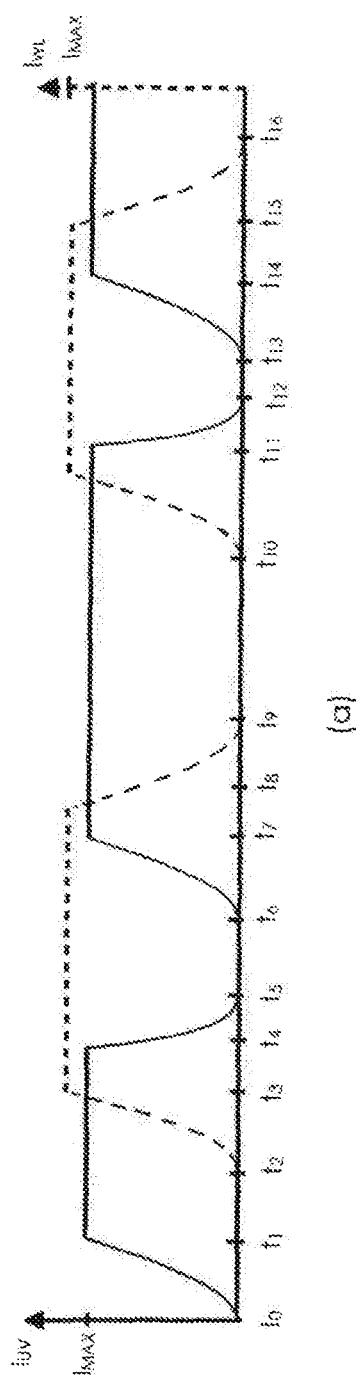
Figure 6:
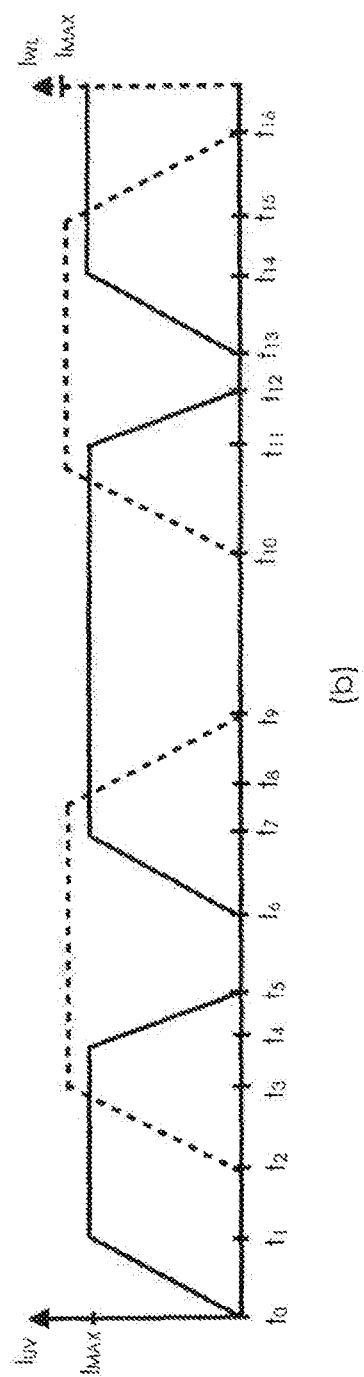

3$^{rd}$ Example (FIG. 6)

As shown in FIG. 6, the UV LED, after the switch-on of the white light LED 3, could also be switched off (points in time $t_4$ and $t_5$) and be switched on again as necessary again to the white light (points in time $t_6$ and $t_7$) for observing the workpiece under UV radiation, the intensity of the white light LEDs 3 is then reduced again (points in time $t_8$ and $t_9$).

Furthermore, FIG. 6 reveals that also when the UV LED 2 is switched on, the intensity can be increased to the target value $I_{MAX}$ gradually, e.g. at one of the speeds described above.

The pushbutton 24 is provided for maintaining respectively attained intensities of the UV LED 2 and of the white light LED 3, i.e. for preventing an illumination state attained with the luminaire 1 from being changed. By way of example, by means of the actuation of the pushbutton 24, the luminaire 1 can be kept in the state at the point in time $t_3$ according to FIG. 4*a* or in the state following point in time $t_3$ according to FIG. 5*a*, without the pushbutton 22 or the pushbutton 22 or 23 having to be kept pressed.

The rotary regulator 25 is provided for varying the target intensity with which the white light LED 3 radiates within certain predetermined limits and for setting it for work with the luminaire 1.

The invention claimed is:

1. A luminaire for testing workpiece surfaces, comprising: at least two illuminants that emit electromagnetic radiation in different wavelength ranges, wherein an intensity with which at least one of the illuminants radiates is adjustable, wherein the luminaire is configured to increase or to reduce the intensity of at least one first of the illuminants and simultaneously keep constant the intensity of at least one other of the illuminants or to reduce or increase the intensity oppositely to the first illuminant.

2. The luminaire according to claim 1, wherein the luminaire is configured for adjusting the intensity at a speed so that a human eye can adapt to a change in the intensity during the adjustment without impairment of visual perception.

3. The luminaire according to claim 2, wherein the luminaire is configured for adjusting the intensity so that a change in the intensity is perceived by the human eye as uniform without intensity jumps.

4. The luminaire according to claim 1, wherein one of the illuminants is configured to emit visible light and another of the illuminants is configured to emit ultraviolet radiation, infrared radiation and/or blue-violet light.

5. The luminaire according to claim 1, further comprising a control and/or regulation device for adjusting the intensity.

6. The luminaire according to claim 1, comprising at least one operating device for changing the intensity.

7. A luminaire for testing workpiece surfaces, comprising: at least two illuminants that emit electromagnetic radiation in different wavelength ranges, wherein an intensity with which at least one of the illuminants radiates is adjustable, wherein the luminaire is configured so that a speed at which the intensity is adjusted is dependent on the intensity with which the respective illuminant radiates.

8. The luminaire according to claim 7, wherein at comparatively low intensity the speed is lower than at comparatively high intensity.

9. A luminaire for testing workpiece surfaces, comprising: at least two illuminants that emit electromagnetic radiation in different wavelength ranges, wherein an intensity with which at least one of the illuminants radiates is adjustable, wherein a speed at which the intensity is changed is between 5 lux/s and 500 lux/s.

10. A luminaire for testing workpiece surfaces, comprising: at least two illuminants that emit electromagnetic radiation in different wavelength ranges, wherein an intensity with which at least one of the illuminants radiates is adjustable, wherein the luminaire is configured for displaying an operating state of at least one of the illuminants, wherein the luminaire is configured for displaying the intensity with which the illuminant emits the radiation, and/or an emission duration.

11. A luminaire for testing workpiece surfaces, comprising: at least two illuminants that emit electromagnetic radiation in different wavelength ranges, wherein an intensity with which at least one of the illuminants radiates is adjustable, further comprising a monitoring device configured to identify and indicate an operational fault.

12. The luminaire according to claim 11, wherein the monitoring device is configured to detect defects in the illuminants and to deactivate the luminaire upon identification of the fault.

13. A method for operating a luminaire having an operating element and at least two illuminants which emit electromagnetic radiation in different wavelength ranges, the method comprising the steps of: increasing or reducing an intensity with which a first one of the illuminants radiates by actuating the operating element; and, simultaneously, either keeping constant or changing oppositely to the first illuminant the intensity with which another illuminant radiates.

14. The method according to claim 13, including increasing or reducing the intensity at a speed so that a human eye is adapted to a change in the intensity during the increasing or reducing ithout impairment of the faculty of sight.

15. A method for operating a luminaire, said luminaire comprising at least two illuminants which emit electromagnetic radiation in different wavelength ranges, the method comprising adjusting an intensity with which at least one of the illuminants radiates, wherein a speed at which the intensity is adjusted is dependent on the intensity with which the respective illuminant radiates.

16. The method according to claim 15, wherein at comparatively low intensity the speed is lower than at comparatively high intensity.

17. A method for operating a luminaire for testing a workpiece surface, said luminaire comprising at least two illuminants which emit electromagnetic radiation in different wavelength ranges, wherein one of the illuminants is configured to emit visible light and another of the illuminants is configured to emit ultraviolet radiation, infrared radiation and/or blue-violet radiation, the method comprising adjusting a radiation intensity of at least one of the illuminants and adjusting a radiation intensity of the luminaire when changing a ratio between illumination with the ultraviolet, the infrared and/or the blue-violet radiation and illumination with the visible light, wherein the radiation intensity of the luminaire is adjusted at a speed so that a human eye is adapted to a change in the intensity during the adjustment without impairment of visual perception.

18. A method for operating a luminaire for testing a workpiece surface, said luminaire comprising at least two illuminants which emit electromagnetic radiation in different wavelength ranges, wherein one of the illuminants is configured to emit to visible light and another of the illuminants is configured to emit ultraviolet radiation, infrared radiation and/or blue-violet radiation, the method comprising adjusting a radiation intensity of at least one of the illuminants and adjusting a radiation intensity of the luminaire when changing a ratio between illumination with the ultraviolet, the infrared and/or the blue-violet radiation and illumination with the visible light, wherein the radiation intensity is adjusted so that a change in the intensity is perceived by a human eye as uniform without intensity jumps.

19. A luminaire for testing workpiece surfaces, comprising: at least two illuminants that emit electromagnetic radiation in different wavelength ranges, wherein one of the illuminants is configured to emit visible light and another of the illuminants is configured to emit ultraviolet radiation, infrared radiation and/or blue-violet radiation, wherein an intensity with which at least one of the illuminants radiates is adjustable, the luminaire being configured for adjusting an intensity with which the luminaire radiates when changing a ratio between illumination with the ultraviolet, the infrared and/or the blue-violet radiation and illumination with the visible light, wherein the luminaire is configured to adjust the intensity at a speed so that a human eye is adapted to a change in the intensity during the adjustment without impairment of visual perception.

20. A luminaire for testing workpiece surfaces, comprising: at least two illuminants that emit electromagnetic radiation in different wavelength ranges, wherein one of the illuminants is configured to emit visible light and another of the illuminants is configured to emit ultraviolet radiation, infrared radiation and/or blue-violet radiation, wherein an intensity with which at least one of the illuminants radiates is adjustable, the luminaire being configured for adjusting an intensity with which the luminaire radiates when changing a ratio between illumination with the ultraviolet, the infrared and/or the blue-violet radiation and illumination with the visible light, wherein the luminaire is configured to adjust the intensity so that a change in the intensity is perceived by a human eye as uniform without intensity jumps.

* * * * *